United States Patent
Ema

(10) Patent No.: US 6,897,948 B2
(45) Date of Patent: May 24, 2005

(54) VARIABLE-WAVELENGTH LIGHT SOURCE APPARATUS

(75) Inventor: Nobuaki Ema, Tokyo (JP)

(73) Assignee: Yokogaw Electric Corporation, Tokyo (JP)

( * ) Notice: Subject to any disclaimer, the term of this patent is extended or adjusted under 35 U.S.C. 154(b) by 675 days.

(21) Appl. No.: 09/933,692

(22) Filed: Aug. 21, 2001

(65) Prior Publication Data

US 2002/0027658 A1 Mar. 7, 2002

(30) Foreign Application Priority Data

Sep. 6, 2000 (JP) ..................................... P.2000-270408

(51) Int. Cl.[7] ............................................. G01M 11/00
(52) U.S. Cl. ................... 356/124.5; 356/125; 356/73.1; 250/227.14; 250/227.19; 250/225
(58) Field of Search ............................... 356/477, 482, 356/73.1, 450, 124, 124.5, 125; 250/227.14, 227.19, 227.22, 225, 227.12

(56) References Cited

U.S. PATENT DOCUMENTS

| | | | | |
|---|---|---|---|---|
| 4,545,253 A | * | 10/1985 | Avicola | ........................ 73/655 |
| 5,227,623 A | * | 7/1993 | Heffner | ........................ 250/225 |
| 5,844,235 A | * | 12/1998 | Tachikawa et al. | ..... 250/227.14 |
| 6,061,124 A | * | 5/2000 | Nyman et al. | ............... 356/124 |
| 6,493,074 B1 | * | 12/2002 | Imamura et al. | .......... 356/124.5 |
| 6,559,946 B2 | * | 5/2003 | Davidson et al. | ........... 356/450 |
| 6,614,511 B1 | * | 9/2003 | Sakairi et al. | ............. 356/73.1 |
| 6,687,008 B1 | * | 2/2004 | Peale et al. | .................. 356/477 |

* cited by examiner

Primary Examiner—Gregory J. Toatley, Jr.
Assistant Examiner—Sang H. Nguyen
(74) Attorney, Agent, or Firm—Fish & Richardson P.C.

(57) ABSTRACT

An optical coupler 13, a reflection attenuation amount measurement photodetector 14, and an APC photodetector 15 are provided in a variable-wavelength light source apparatus 1 and the reflection attenuation amount can be measured simply by connecting a device under test without using any external optical power meter, etc, and when wavelength calibration is executed, an external wavelength calibration gas cell 18 and a total reflection termination 20 are connected, whereby the wavelength of an optical signal output from a variable-wavelength light source 11 can be measured and controlled with higher accuracy.

7 Claims, 3 Drawing Sheets

VARIABLE-WAVELENGTH LIGHT SOURCE APPARATUS

BACKGROUND OF THE INVENTION

1. Field of the Invention

This invention relates to a variable-wavelength light source apparatus used for evaluating and manufacturing an optical communication system and an optical device.

2. Description of the Related Art

Hitherto, a variable-wavelength light source (a tunable laser source) capable of varying a wavelength of output light has been used as a main component for outputting test signals to test an optical part in measurement, adjustment, study, etc., of the optical part. FIG. 3 shows a configuration example of an optical parts measurement apparatus 100 for measuring optical characteristics of an optical part using a variable-wavelength light source according to a related art.

The optical parts measurement apparatus 100 comprises a variable-wavelength light source 101, an optical coupler 102, optical fibers 103, 104, and 105, and an optical power meter 107. The optical coupler 102 has three output terminals 108, 109, and 110 and the output terminal 108 or 109 is connected to the optical power meter 107 by the optical fiber 104. The output terminals 108 and 109 can be selectively connected to the optical power meter 107. In case of connecting the optical power meter 107 to the output terminal 109, the intensity of an optical signal output from the variable-wavelength light source 101 to the optical coupler 102 is measured. In case of connecting the optical power meter 107 to the output terminal 108, the intensity of a light reflection signal input to the optical coupler 102 as return light reflected from a device under test 106 is measured. The device under test 106 of an optical part is connected to the output terminal 110 by the optical fiber 105.

When an optical signal is output via the optical fiber 103 from the variable-wavelength light source 101, the optical signal is branched through the optical coupler 102 to the output terminals 109 and 110. The optical signal branched to the output terminal 109 of the optical coupler 102 is input via the optical fiber 104 to the optical power meter 107 previously connected to the output terminal 109 (if the optical fiber 104 is connected to the output terminal 109 rather than the output terminal 108). The intensity of the optical signal output from the variable-wavelength light source 101 is measured with the optical power meter 107.

The optical signal branched to the output terminal 110 is input via the optical fiber 105 to the device under test 106 and is transmitted, reflected, or scattered by various optical elements provided in the device under test 106. The light reflection signal reflected by the device under test 106 is again input to the optical coupler 102 via the optical fiber 105.

The light reflection signal input to the optical coupler 102 is output to the output terminal 108 of the optical coupler 102. The optical fiber 104 and the optical power meter 107 connected to the output terminal 109 are changed to connection to the output terminal 108 from connection to the output terminal 109, whereby the light reflection signal is input to the optical power meter 107 via the optical fiber 104 and the intensity of the light reflection signal is measured. The previously measured intensity of the optical signal from the variable-wavelength light source 101 is compared with the intensity of the light reflection signal of return light from the device under test 106, thereby measuring a light reflection attenuation amount of the device under test 106. Measuring is repeated while a wavelength of the optical signal output from the variable-wavelength light source 101 is changed, whereby wavelength characteristic of the light reflection attenuation amount of the device under test 106 can be measured.

The variable-wavelength light source 101 according to the related art contains a gas cell for wavelength calibration (not shown), whereby the wavelength of the optical signal output from the variable-wave-length light source 101 is monitored, is measured, and calibrated.

However, in relation to the variable-wavelength light source according to the related art, when the optical part is measured, the external power meter needs to be attached through the optical coupler and connection of the optical power meter must be changed at each time measurement. The measurement takes labor and time and is cumbersome, and thus this is a problem.

The variable-wavelength light source needs to output an optical signal having a longer wavelength and an optical signal having a shorter wavelength with high precision and high accuracy of an optical part in recent years. Thus, it is a problem that the gas cell for wavelength calibration contained in the variable-wavelength light source according to the related art cannot deal with longer or shorter wavelengths. In case of using an external gas cell for wavelength calibration capable of dealing with long and short wavelengths, an additional external optical power meter, etc., needs to be installed. Thus, it is problem that this takes labor, time, and costs.

SUMMARY OF THE INVENTION

It is an object of the invention to provide a variable-wavelength light source apparatus that can easily measure the light reflection attenuation amount of an optical part simply by connecting a device under test to the variable-wavelength light source apparatus and can also deal strictly with a wider wavelength range.

The invention according to a first aspect is a variable-wavelength light source apparatus (for example, a wavelength light source unit 1 in FIG. 1) for generating a measurement optical signal from a measurement light source and outputting the optical signal to an optical device, said variable-wavelength light source apparatus comprising:

a light branching unit for branching the measurement optical signal to a plurality optical signals and outputting the plurality of optical signals to predetermined output terminals (for example, an optical coupler 13 shown in FIG. 1);

a light reflection signal output unit for outputting a light reflection signal input from the optical device to a predetermined output terminal (for example, an optical coupler 13 shown in FIG. 1);

a first light reception device for receiving branch light output by said light branch unit to convert the branch signal into an electric signa (for example, a APC photodetector 15 shown in FIG. 1)1; and a second light reception device for receiving the light reflection signal output by said light reflection signal output unit to convert the light reflection signal into an electric signal (for example, a reflection attenuation amount measurement photodetector 14 shown in FIG. 1).

According to the first aspect of the invention, in the variable-wavelength light source apparatus for generating the measurement optical signal from the measurement light source and outputting the measurement optical signal to the optical device, the light branch unit branches the measurement optical signal to the plurality of optical signals and outputs the plurality of optical signals to the predetermined output terminals, the light reflection signal output unit outputs the light reflection signal input from the optical device to the predetermined output terminal, and there are provided the first light reception device which receives the branch light output by the light branch unit to convert the branch signal into the electric signal and the second light reception device which receives the light reflection signal output by the light reflection signal output unit to convert the light reflection signal into the electric signal, so that the light reflection attenuation amount of the device under test can be measured without using any external power meter, etc. Thus, the labor, time, and the costs in measurement can be saved and the measurement time can also be shortened.

The invention according to a second aspect is the variable-wavelength light source apparatus according to the first aspect of the invention, wherein the light branch unit and the light reflection signal output unit are optical couplers having a plurality of output terminals (for example, the optical coupler 13 shown in FIG. 1); and the first light reception device, the second light reception device, and the optical device are connected to the plurality of output terminals at the same time.

According to the second aspect of the invention, the light branch unit and the light reflection signal output unit are the optical couplers having the plurality of output terminals, and the first light reception device, the second light reception device, and the optical device are connected to the plurality of output terminals at the same time. Thus, measurement can be executed without changing connection of the photodetector, etc., at each time, so that the labor and time in measurement can be saved and the measurement time can be shortened. The intensities of the optical signal output from the variable-wavelength light source and the light reflection signal output from the device under test can be measured at the same time, so that measurement with higher accuracy can be conducted.

The invention according to a third aspect is the variable-wavelength light source apparatus according to anyone of the first and the second aspects of the invention, wherein the optical device is one of a measured optical part (for example, a device under test 17 shown in FIG. 1) and a wavelength calibration gas cell (for example, wavelength calibration gas cell 18 shown in FIG. 2) connected to a total reflection termination (for example, a total reflection terminal 20 shown in FIG. 2); and a wavelength of the measurement optical signal output from the measurement light source is calibrated using the wavelength calibration gas cell connected to the total reflection termination.

According to the third aspect of the invention, the optical device is one of the measured optical part and the wavelength calibration gas cell connected to the total reflection termination, and the wavelength of the measurement optical signal output from the measurement light source is calibrated using the wavelength calibration gas cell connected to the total reflection termination, so that the wavelength of the optical signal output from the variable-wavelength light source can be calibrated more accurately without using any external optical power meter, etc. Therefore, highly reliable measurement can be conducted without taking costs, labor, or time, etc. Since the wavelength calibration gas cell and the total reflection termination are external devices, the variable-wavelength light source apparatus can deal with any wavelength by replacing the wavelength calibration gas cell in response to the measurement optical signal output from the variable-wavelength light source. Thus, the measured optical part can be measured using a more accurate measurement signal.

The invention according to a fourth aspect is a variable-wavelength light source apparatus comprising:

an light source for emitting a measurement light signal;

an optical coupler having a plurality of input/output terminals;

a first light reception device for receiving a light signal to convert into an electric signal; and a second light reception device for receiving a light signal to convert into an electric signal, wherein the optical coupler is input the measurement optical signal, and branches the measurement optical signal into a first and a second branched optical signals to output the first and second branched optical signals to an optical device and the first light reception device, respectively, and is input a reflection light signal reflected by the optical device to output the reflection light signal to the second light reception device.

The invention according to a fifth aspect is the variable-wavelength light source apparatus according to the fourth aspect of the invention, wherein the plurality of input/output terminals are four input/output terminals.

The invention according to a sixth aspect is the variable-wavelength light source apparatus according to the fourth aspect of the invention, wherein the light source varies a wavelength of the measurement light signal.

The invention according to a seventh aspect is the variable-wavelength light source apparatus according to the fourth aspect of the invention, wherein the first and the second light reception devices and the optical device are connected to the optical coupler at the same time.

The invention according to an eighth aspect invention is the variable-wavelength light source apparatus according to the fourth aspect of the invention, wherein the optical device is one of a measured optical part and a wavelength calibration gas cell connected to a total reflection termination for calibrating a wavelength of the measurement light signal.

The invention according to a ninth aspect is the variable-wavelength light source apparatus according to the eighth aspect of the invention, wherein the wavelength calibration gas cell is detachably connected to the optical coupler; and the optical coupler has an absorption wavelength range corresponding to a wavelength of the measurement optical signal.

DETAILED DESCRIPTION OF THE PREFERRED EMBODIMENTS

[First embodiment]

Referring now to the accompanying drawings, preferred embodiments of the invention will be given specifically.

Figure 1:
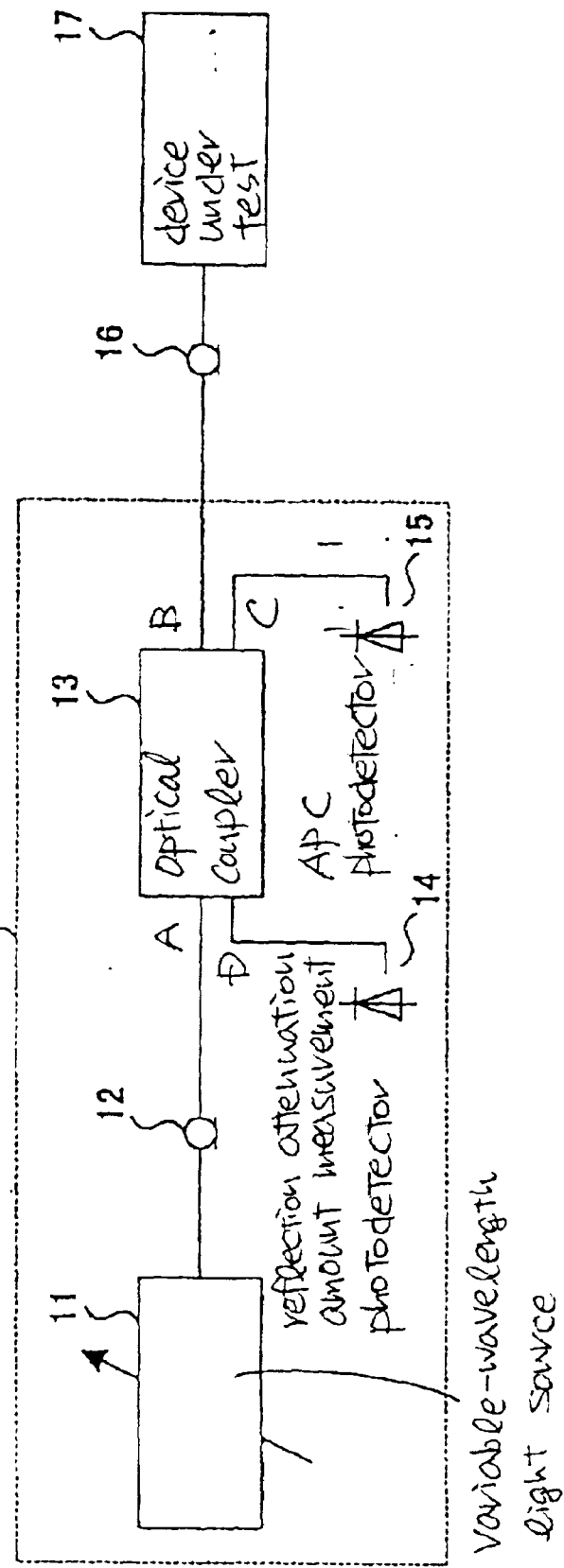
FIG. 1 is a block diagram to show a configuration of a main part of a variable-wavelength light source apparatus 1 to which a first embodiment of the invention is applied.

FIG. 1 is a diagram to show a variable-wavelength light source apparatus 1 to which a first embodiment of the invention is applied.

First, a configuration of the variable-wavelength light source apparatus 1 will be discussed.

FIG. 1 is a block diagram to show a configuration of a main part of the variable-wavelength light source apparatus 1 according to the first embodiment of the invention. In FIG. 1, the variable-wavelength light source apparatus 1 is constructed of a variable-wavelength light source 11, an optical fiber 12, an optical coupler 13, a reflection attenuation amount measurement-photodetector 14, and an APC (autopower control) photodetector 15. The optical coupler 13 has terminals A, B, C, and D. The variable-wavelength light source 11 is connected to the terminal A via the optical fiber 12 and an optical signal output from the variable-wavelength light source 11 is input through the terminal A. The reflection attenuation amount measurement photodetector 14, the APC photodetector 15, and a device under test 17 via an optical fiber 16 are connected to the terminals D, C, and B, respectively, at the same time.

The variable-wavelength light source 11 outputs the optical signal for applying a test signal to the device under test 17. A semiconductor laser or a light emitting diode is used as the light source and the wavelength and the output intensity of the optical signal to be output can be variably set as desired in response to the device under test and a measurement condition. The optical signal output from the variable-wavelength light source 11 is input to the terminal A of the optical coupler 13 via the optical fiber 12.

The optical coupler 13 branches the optical signal input from the variable-wavelength light source 11 to output the branched optical signals from the output terminals C and B, respectively. The optical signals output from the terminals C and B of the optical coupler 13 are input to the APC photodetector 15 and the device under test 17 through the optical fiber 16, respectively. The optical coupler 13 is input a light reflection signal reflected at the device under test 17 to output the light reflection signal from the terminal D to the reflection attenuation amount measurement photodetector 14.

The reflection attenuation amount measurement photodetector 14 measures the intensity of the light reflection signal reflected at the device under test 17. Of the light signal input to the device under test 17, return light reflected by an optical element in the device under test 17 is input to the terminal B of the optical coupler 13 as the light reflection signal. The light reflection signal is input through the terminal D of the optical coupler 13 to the reflection attenuation amount measurement photodetector 14 to convert the light reflection signal into an electric signal, thereby detecting the intensity of the light reflection signal.

The APC photodetector 15 detects the intensity of the optical signal output from the variable-wavelength light source 11; the APC photodetector 15 detects the intensity of the optical signal branched by the optical coupler 13 to be output from the terminal C.

The device under test 17 is an optical part having various optical elements, for example, a light module, a light splitter, a light circulator, etc. The light signal from the variable-wavelength light source 11, branched by the optical coupler 13 is input to the device-under test 17 via the optical fiber 16.

Next, a reflection attenuation amount measurement operation of the device under test 17 executed in the variable-wavelength light source apparatus 1 according to the embodiment will be discussed.

The optical signal output from the variable-wavelength light source 11 is previously set the output intensity, the wavelength, etc., in response to the device under test 17 and the measurement condition, and is output to the optical coupler 13 via the optical fiber 12.

The optical signal output to the optical coupler 13 is branched to the two output terminals to be output from the terminals B and C, respectively and the optical signals are input to the APC photodetector 15 and the device under test 17 via the optical fiber 16, respectively. The optical intensity of the optical signal input to the APC photodetector 15 is detected.

The optical signal input to the device under test 17 is transmitted, reflected, and scattered by each of various optical elements provided in the device under test 17. The return light reflected by the optical elements in the device under test 17 is input to the terminal B of the optical coupler 13 as the light reflection signal via the optical fiber 16. The light reflection signal is output from the terminal D of the optical coupler 13 to the reflection attenuation amount measurement photodetector 14 and the optical intensity of the light reflection signal is detected.

The intensity of the optical signal detected by the APC photodetector 15 is compared with the intensity of the light reflection signal detected by the reflection attenuation amount measurement photodetector 14, whereby the reflection attenuation amount of the device under test 17 is measured.

Thus, the variable-wavelength light source apparatus 1 according to the first embodiment provides the following advantages.

Since the function of measuring the light reflection attenuation amount of the optical part is further provided in the variable-wavelength light source apparatus, the light reflection attenuation amount can be measured simply by connecting the device under test on which measurement is to be conducted to the variable-wavelength light source apparatus without using any external power meter, etc. Thus, the labor, time, and the costs in measurement can be saved and the measurement time can also be shortened.

The optical coupler having the plurality of output terminals is installed in the variable-wavelength light source apparatus for branching the optical signal to output the branched optical signals from the output terminals, whereby the reflection attenuation amount measurement photodetector, the APC photodetector, and the device under test can be connected at the same time. Thus, the reflection attenuation amount of the device under test can be measured simply by comparing the intensity of the optical signal detected by the APC photodetector with the intensity of the light reflection signal detected by the reflection attenuation amount measurement photodetector. Therefore, measurement can be executed without changing connection of the photodetector, etc., at each time, so that the labor and time in measurement can be saved and the measurement time can be shortened.

The intensities of the optical signal output from the variable-wavelength light source and the light reflection signal output from the device under test can be measured at the same time, so that measurement with higher accuracy can be conducted.

The configuration of the variable-wavelength light source apparatus 1 shown in the embodiment is one example and the number of the input/output terminals of the optical coupler 13, the connection form of the photodetector, etc., can be changed without departing from the spirit and the scope of the embodiment of the invention.

[Second embodiment]

Next, a second embodiment of the invention will be discussed with reference to FIG. 2.

Figure 2:
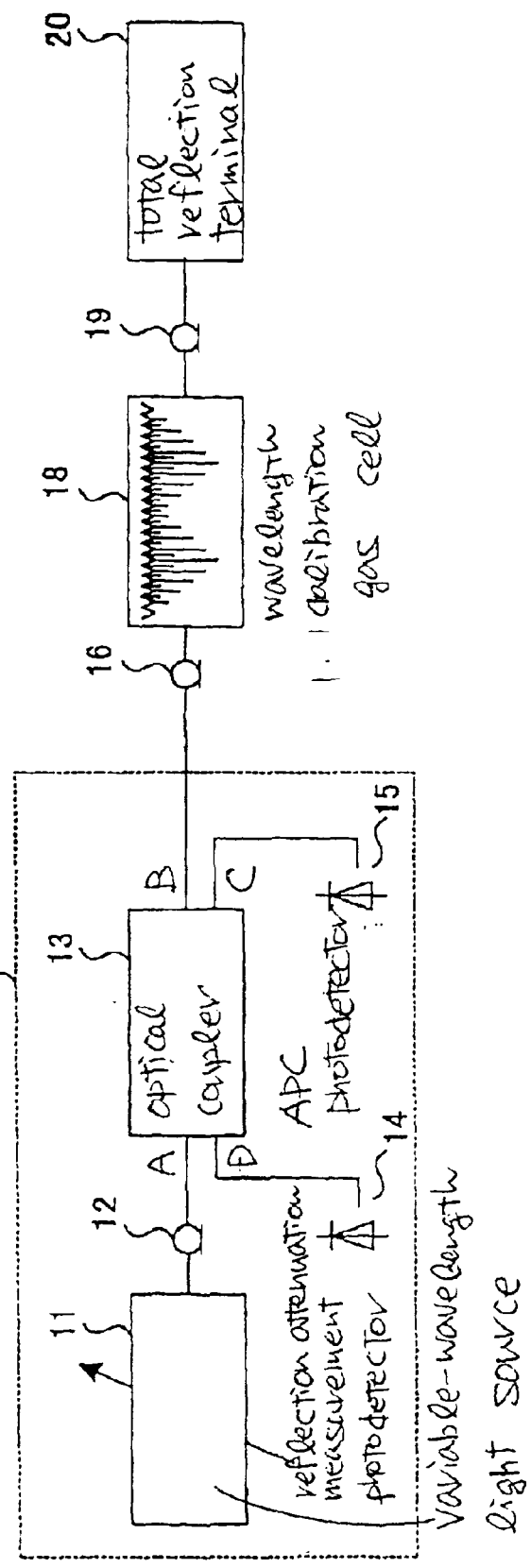
FIG. 2 is a block diagram to show a configuration of a main part of a variable-wavelength light source apparatus 1 to which a second embodiment of the invention is applied.
Figure 3:
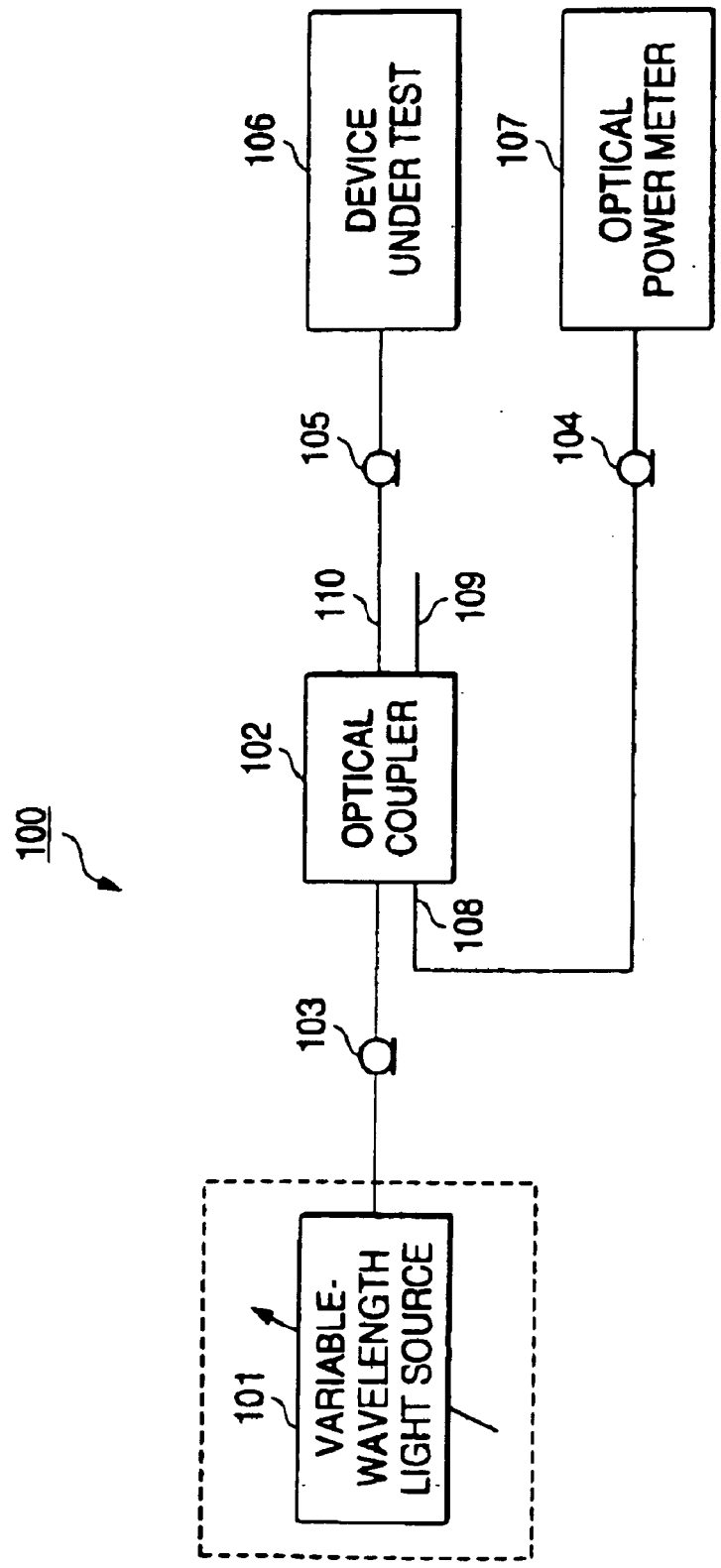
FIG. 3 is a block diagram to show a configuration of a main part of an optical parts measurement apparatus 100 using a variable-wavelength light source 101 in a related art.

FIG. 2 is a block diagram to show a configuration of a main part of a variable-wavelength light source apparatus 1 according to a second embodiment of the invention. Parts identical with those previously described with reference to FIG. 1 are denoted by the same reference numerals in FIG. 2 and will not be given again.

The variable-wavelength light source apparatus 1 according to the second embodiment of the invention shown in FIG. 2 differs from the variable-wavelength light source apparatus 1 according to the first embodiment of the invention previously described with reference to FIG. 1 mainly in that a wavelength calibration gas cell 18 and a total reflection termination 20 are connected to the variable-wavelength light source apparatus 1 in place of the device under test 17.

The output intensity, the wavelength, and the like of a variable-wavelength light source 11 can be set as desired. Thus, to realize a stricter measurement condition, it needs to measure an optical signal output from the variable-wavelength light source 11 by a wavelength calibration gas cell, etc., for calibrating the wavelength of the optical output signal.

In the second embodiment, the wavelength calibration gas cell 18 is installed to monitor the wavelength of an optical signal output from the variable-wavelength light source 11. Gas for absorbing light in a specific frequency range or a large number of frequency ranges, such as cyan gas or acetylene gas, is sealed in the wavelength calibration gas cell 18. Light is passed through the wavelength calibration gas cell 18, whereby the light absorption characteristic of the gas is used to measure and control the optical signal output from the variable-wavelength light source 11.

The total reflection termination 20 totally reflects the optical signal of a specific wavelength output from the wavelength calibration gas cell 18 via an optical fiber 19 and returns the optical signal to the wavelength calibration gas cell 18.

The wavelength calibration operation executed in the variable-wavelength light source apparatus 1 according to the second embodiment will be discussed.

The optical signal output from the variable-wavelength light source 11 is output to a terminal A of an optical coupler 13 via an optical fiber 12. The optical signal input to the terminal A of the optical coupler 13 is branched to be output to terminals C and B of the optical coupler 13, and the branched optical signals are input to an APC photodetector 15 and the wavelength calibration gas cell 18 via an optical fiber 16. The optical intensity of the optical signal input to the APC photodetector 15 is detected.

As for the light signal input to the wavelength calibration gas cell 18, only a specific optical signal is passed through based on the absorption characteristic of the sealed-in gas and is output to the total reflection termination 20. A light reflection signal totally reflected by the total reflection termination 20 is again passed through the wavelength calibration gas cell 18 and is input via the optical coupler 13 to a reflection attenuation amount measurement photodetector 14 for detecting the optical intensity of the light reflection signal.

The intensity of the optical signal detected by the APC photodetector 15 is compared with the intensity of the light reflection signal detected by the reflection attenuation amount measurement photodetector 14, and wavelength calibration and control of the optical signal output from the variable-wavelength light source 11 are performed.

Thus, according to the second embodiment, in addition to the advantage of the first embodiment, the wavelength of the optical signal output from the variable-wavelength light source 11 can be calibrated more accurately without using any external optical power meter, etc. Therefore, highly reliable measurement can be conducted without taking costs or labor, time, etc.

Since the wavelength calibration gas cell is an external gas cell, the optical signal can be calibrated simply by replacing the wavelength calibration gas cell in response to any wavelength output from the variable-wavelength light source. That is, in recent years, demand for using the variable-wavelength light source in a wide band (wide wavelength range) from a long wavelength to a short wavelength has been increasing. According to the second embodiment, any appropriate wavelength calibration gas cell in the widened wavelength range can be selected, so that an optical signal of a precise wavelength in a wide band can be output.

After measurement terminates, the wavelength calibration gas cell is removed from the variable-wavelength light source and is stored separately, whereby measurement can be conducted with more safety.

The configuration of the variable-wavelength light source apparatus 1 shown in the embodiment is one example and the number of the output terminals of the optical coupler, the number of the optical fibers, etc., can be changed without departing from the spirit and the scope of the embodiment of the invention.

According to the variable-wavelength light source apparatus of the first aspect of the invention, the function of measuring the reflection attenuation amount is further provided in the variable-wavelength light source apparatus, so that the light reflection attenuation amount of the device under test can be measured without using any external power meter, etc., simply by connecting the device under test on which measurement is to be conducted to the variable-wavelength light source apparatus. Thus, the labor, time, and the costs in measurement can be saved and the measurement time can also be shortened.

According to the variable-wavelength light source apparatus of the second aspect of the invention, the optical coupler having a plurality of output terminals is installed and the reflection attenuation amount measurement photodetector, the APC photodetector, and the device under test are connected at the same time. Thus, measurement can be executed without changing connection of the photodetector, etc., each time it is conducted, so that the labor and time in measurement can be saved and the measurement time can be shortened.

The intensities of the optical signal output from the variable-wavelength light source and the light reflection signal output from the device under test can be measured at the same time, so that measurement with higher accuracy can be conducted.

According to the variable-wavelength light source apparatus of the invention of the third aspect of the invention, the wavelength of the optical signal output from the variable-wavelength light source can also be calibrated more accurately without using any external optical power meter, etc., as in measurement on the device under test. Therefore, highly reliable measurement can be conducted without taking costs or labor, time, etc. Since the wavelength calibration gas cell is an external gas cell, the optical signal can be calibrated simply by replacing the wavelength calibration gas cell in response to any wavelength output from the variable-wavelength light source.

What is claimed is:

1. A variable-wavelength light source apparatus for generating a measurement optical signal from a measurement light source and outputting the optical signal to an optical device, said variable-wavelength light source apparatus comprising:

a light branching unit for branching the measurement optical signal to a plurality of optical signals and outputting the plurality of optical signals to predetermined output terminals;

a light reflection signal output unit for outputting a light reflection signal input from the optical device to a predetermined output terminal;

a first light reception device for receiving branch light output by said light branch unit to convert the branch signal into an electric signal; and a second light reception device for receiving the light reflection signal output by said light reflection signal output unit to convert the light reflection signal into an electric signals;

wherein the optical device is one of a measured optical part and a wavelength calibration gas cell connected to a total reflection termination; and wherein a wavelength of the measurement optical signal output from the measurement light source is calibrated using the wavelength calibration gas cell connected to the total reflection termination.

2. The variable-wavelength light source apparatus according to claim 1 wherein said light branch unit and said light reflection signal output unit are optical couplers having a plurality of output terminals; and said first light reception device, said second light reception device, and the optical device are connected to the plurality of output terminals at the same time.

3. A variable-wavelength light source apparatus comprising:

a light source for emitting a measurement light signal;

an optical coupler having a plurality of input/output terminals;

a first light reception device for receiving a light signal to convert into an electric signal; and a second light reception device for receiving a light signal to convert into an electric signal, wherein the optical coupler is input the measurement optical signal, and branches the measurement optical signal into a first and a second branched optical signals to output the first and second branched optical signals to an optical device and the first light reception device, respectively, and is input a reflection light signal reflected by the optical device to output the reflection light signal to the second light reception device; and wherein the optical device is one of a measured optical part and a wavelength calibration gas cell connected to a total reflection termination for calibrating a wavelength of the measurement light signal.

4. The variable-wavelength light source apparatus according to claim 3, wherein the plurality of input/output terminals are four input/output terminals.

5. The variable-wavelength light source apparatus according to claim 3, wherein the light source varies a wavelength of the measurement light signal.

6. The variable-wavelength light source apparatus according to claim 3, wherein the first and the second light reception devices and the optical device are connected to the optical coupler at the same time.

7. The variable-wavelength light source apparatus according to claim 3, wherein the wavelength calibration gas cell is detachably connected to the optical coupler; and the optical coupler has an absorption wavelength range corresponding to a wavelength of the measurement optical signal.

* * * * *